(12) United States Patent
Kocjancic et al.

(10) Patent No.: US 9,314,322 B2
(45) Date of Patent: Apr. 19, 2016

(54) DEVICE AND METHOD FOR MEASURING PRESSURE EXERTED ON A SURFACE

(75) Inventors: Ervin Kocjancic, Chicago, IL (US); Craig S. Niederberger, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 375 days.

(21) Appl. No.: 13/696,949

(22) PCT Filed: May 11, 2011

(86) PCT No.: PCT/US2011/036083
§ 371 (c)(1),
(2), (4) Date: Feb. 28, 2013

(87) PCT Pub. No.: WO2011/143316
PCT Pub. Date: Nov. 17, 2011

(65) Prior Publication Data
US 2013/0158436 A1    Jun. 20, 2013

Related U.S. Application Data

(60) Provisional application No. 61/333,824, filed on May 12, 2010.

(51) Int. Cl.
*A61B 5/20* (2006.01)
*A61F 2/00* (2006.01)
(Continued)

(52) U.S. Cl.
CPC .............. *A61F 2/0045* (2013.01); *A61B 5/0053* (2013.01); *A61B 5/03* (2013.01);
(Continued)

(58) Field of Classification Search
CPC ........ A61B 1/307; A61B 5/03; A61B 5/0053; A61B 5/20; A61B 5/205; A61B 5/6885; A61B 5/6806; A61B 2562/0247; A61B 2562/247; A61F 2/0045
USPC ................. 128/898, DIG. 25; 600/29, 30, 37, 600/587–595
See application file for complete search history.

(56) References Cited

U.S. PATENT DOCUMENTS 4,414,984 A   11/1983   Zarudiansky
5,010,772 A   4/1991    Bourland et al.
(Continued)

FOREIGN PATENT DOCUMENTS

WO    WO 2008/131557    11/2008

OTHER PUBLICATIONS

Oshana, Robert. (2006). DSP Software Development Techniques for Embedded and Real-Time Systems. Elsevier. Chapter 2. Retrieved from <http://app.knovel.com/hotlink/toc/id:kpDSPSDTE1/dsp-software-development/dsp-software-development> on Nov. 13, 2014.*

(Continued)

*Primary Examiner* — Devin Henson
*Assistant Examiner* — David J McCrosky
(74) *Attorney, Agent, or Firm* — Lathrop & Gage LLP

(57) ABSTRACT

Provided are methods and devices for measuring pressure exerted against a surface. In an aspect, the surface corresponds to the urethra and the device measures the pressure exerted against the urethra. Methods include treatment of a patient suffering urinary stress incontinence. A pressure sensor system is used to determine, pre-surgically, the minimum pressure required to alleviate incontinence. During surgery, the pressure sensor system is employed to ensure the surgical intervention provides a corresponding minimum pressure that was clinically identified. In this manner, the surgical intervention is precisely monitored and measured to insure the appropriate pressure is exerted on the urethra to alleviate stress incontinence, thereby improving surgical outcome and decreasing post-operative complications.

9 Claims, 11 Drawing Sheets

(51) Int. Cl.
A61B 5/03 (2006.01)
A61B 5/00 (2006.01)

(52) U.S. Cl.
CPC .................. *A61B 5/20* (2013.01); *A61B 5/205* (2013.01); *A61B 5/4851* (2013.01); *A61B 5/6806* (2013.01); *A61B 5/6874* (2013.01); *A61B 5/6885* (2013.01); *A61B 5/686* (2013.01); *A61B 5/6852* (2013.01); *A61B 2562/0247* (2013.01); *A61B 2562/247* (2013.01)

(56) References Cited

U.S. PATENT DOCUMENTS

| | | | |
|---|---|---|---|
| 6,019,423 | A | 2/2000 | Dodge et al. |
| 6,272,936 | B1 | 8/2001 | Oreper et al. |
| 6,302,840 | B1 | 10/2001 | Benderev |
| 6,450,046 | B1 * | 9/2002 | Maeda ..................... 73/862.473 |
| 6,743,165 | B2 | 6/2004 | Mosel et al. |
| 6,807,869 | B2 | 10/2004 | Farringdon et al. |
| 6,964,205 | B2 | 11/2005 | Papakostas et al. |
| 7,258,026 | B2 | 8/2007 | Papakostas et al. |
| 7,845,225 | B2 | 12/2010 | Ridenour et al. |
| 2003/0009181 | A1 | 1/2003 | Gellman |
| 2009/0058661 | A1 | 3/2009 | Gleckler et al. |
| 2010/0069784 | A1 | 3/2010 | Blaivas |
| 2010/0292615 | A1 | 11/2010 | Niederberger |

OTHER PUBLICATIONS

Albert, C.L. et al. (2004). Fundamentals of Industrial Control (2nd Edition). The Instrumentation, Systems and Automation Society. Sect. 1.5.7. Retrieved from <http://app.knovel.com/hotlink/toc/id:kpFICE000N/fundamentals-industrial/fundamentals-industrial> on Aug. 19, 2015.*

Kocjancic, E. et al. (Apr. 2010). Adjustable continence therapy (ProAct®) for men stress urinary incontinence: Long term results. Journal of Urology, 183(4), e620, Abstract. doi:http://dx.doi.org/10.1016/j.juro.2010.02.1384.*

Benjamin, B.E. (2004) "Cycling and Your Health," *Massage Therapy J.*

Blakeslee, S. (Oct. 4, 2005) "Serious Riders, Your Bicycle Seat May Affect Your Love Life/Strong," *New York Times*.

Breda et al. (2005) "Development of a New Geometric Bicycle Saddle for the Maintenance of Genital-Perineal Vascular Perfusion," *J. Sex. Med.* 2:605-611.

Forghani et al. (May 2008) "Design and Fabrication of a Device Measuring Perineal Pressures Real-Time During Bicycle Riding to Determine Erectile Dysfunction Risk," Poster Presented at the 2008 Annual Meeting of the American Urological Association; May 17-22, Orlando Florida.

Forghani et al. (May 19, 2008) "Design and Fabrication of a Device Measuring Perineal Pressures Real-Time During Bicycle Riding to Determine Erectile Dysfunction Risk," *J. Urology* 179(4)Supplement:281 Abstract # 809.

Huang et al. (2005) "Bicycle Riding and Erectile Dysfunction: An Increase in Interest (and Concern)," *J. Sex. Med.* 2:596-604.

International Search Report and Written Opinion for PCT application PCT/US11/36083 Aug. 15, 2011—8 pages.

Lowe et al. (2004) "Effects of Bicycle Saddle Designs on the Pressure to the Perineum of the Bicyclist," *Med. Sci. Sports Exerc.* 36(6):1055-1062.

Munarriz et al. (2005) "Only the Nose Knows: Penile Hemodyamic Study of the Perineum-Saddle Interface in Men with Erectile Dysfunction Utilizing Bicycle Saddles and Seats with and Without Nose Extensions," *J. Sex. Med.* 2:612-619.

National Institute for Occupational Safety and Health Report (2009) "No-Nose Saddles for Preventing Genital Numbness and Sexual Dysfunction from Occupational Bicycling," Niosh Pub. No. 2009-131.

Novel "Pliance Saddle Systems," http://www.novel.de/old/nav2/nav_215.htm, Accessed Apr. 5, 2010.

Schrader et al. "Your Health and Bike Seats," Spongy Wonder Bicycle Seats, http://www.Spongywonder.com/Yourhealth.htm, Accessed Apr. 5, 2010.

Schrader et al. (2008) "Cutting Off the Nose to Save the Penis," *J. Sex. Med.* 5:1932-1940.

Schrader et al. (2002) "Nocturnal Penile Tuminescnece and Rigidity Testing in Bicycling Patrol Offices," *J. Andrology* 23(6):927-934.

Sommer et al. (2001) "Erectile Dysfunction in Cyclists," *Eur. Urol.* 39(6):720-723.

Tekscan (Feb. 5, 2009) "FlexiForce® Sensors User Manual," http://www.tekscan.com/pdf/FlexiForce-Sensors-Manual.pdf.

Extended European Search Report corresponding to European Patent Application No. 11781209.9, dated Jul. 18, 2014.

* cited by examiner

DEVICE AND METHOD FOR MEASURING PRESSURE EXERTED ON A SURFACE

CROSS-REFERENCE TO RELATED APPLICATIONS

This application is a national stage application under 35 U.S.C. §371 of PCT/US2011/036083, filed May 11, 2011, which claims the benefit of U.S. provisional application 61/333,824 filed May 12, 2010, each of which is incorporated by reference in its entirety to the extent not inconsistent with the disclosure herein.

BACKGROUND OF THE INVENTION

Provided herein are various devices and methods that measure the pressure or force exerted against a surface. One application of the devices and methods provided herein are for surgical procedures that address urinary incontinence, including female stress incontinence.

Urinary incontinence occurs in both men and women and is typically associated with unwanted urinary leakage that occurs with abdominal pressure increases such as from sneezing, coughing, hiccupping, exercise, laughing and other such stimuli. Interventions to address urinary incontinence include surgical procedures. Many procedures involve a surgical injection and placement of a material to mechanically support the bladder neck or the urethra.

Some studies suggest it is beneficial to use pressure-sensing catheters to simultaneously measure a patient's vesicle and urethral pressure (see, e.g., U.S. Pat. No. 6,743,165). Common procedures for surgically alleviating stress incontinence relate to supporting the urethra by employing materials to physically support the urethra, such as sutures, straps, slings or other artificial structures that loop around the urethra. Those materials may be attached to adjacent tissue, bone, ligament or other support material. For example, a sling may be looped around the urethra and connected to the pubis and around the obturator foramen. The problem with those interventions, however, is that the actual pressure exerted on the urethra is unknown.

SUMMARY OF THE INVENTION

Provided herein are various devices and methods for measuring the pressure exerted on a surface. In an aspect, the surface corresponds to biological tissue or organ such as the surface of a vessel or organ. In an embodiment the surface is the surface of the urethra. The methods and devices are further useful for treating urinary stress incontinence. The devices and methods provided herein are useful for detecting in real-time an "active" pressure or force exerted against a biological tissue, such as that provided by a finger or hand of a medical caregiver, or a medical device that is being implanted or used with a patient. Alternatively, the methods and devices provided herein are used to detect in real-time a "passive" pressure or force exerted between a patient and a surface, such as between one or more locations on the patient's skin or body and a surface such as a support surface, including a bed or operating table.

With respect to an application for treating urinary stress incontinence, conventional methods for assessing and treating stress incontinence are rudimentary and suffer serious drawbacks. Current methodologies for treating incontinence generally involve a crude compression of the urethra in clinic to determine if stress incontinence can be cured. Those methods, however, do not use a device to accurately determine the magnitude of pressure required to attain continence. If the crude clinical test is positive, the patient undergoes an operation where an artificial structure is introduced to exert a supporting pressure on the urethra. Once again, however, there is no measure of the actual pressure exerted on the urethra. This means that the surgeon has no reliable method for ensuring the pressure exerted on the urethra by the structure corresponds to the pressure exerted pre-surgically that alleviated incontinence. Serious complications can arise when the surgically-imparted force on the urethra is not appropriate to the minimum pressure required to alleviate incontinence. If the pressure is too low, recurrent stress incontinence may occur, requiring additional invasive intervention. If the pressure is too high, the sling may prematurely erode and there may be an increased risk of infection, which may require, again, additional surgical intervention. The methods provided herein solve this problem by providing a mechanism for ensuring an appropriate pressure is exerted on the urethra to treat stress incontinence and provide improved clinical outcome.

The devices provided herein (see also U.S. Pat. App. No. 61/177,583 and U.S. Pat. Pub. No. 20100292615, hereby specifically incorporated by reference for the devices and methods disclosed therein), provide the ability to accurately monitor and measure a force (or a corresponding pressure) exerted on any surface, including, for example, the urethra. In an aspect, the required force and pressure required in the clinic to alleviate incontinence are determined with the device, and the device is then used during surgery to ensure the pressure of the introduced supporting device on the urethra during surgery is correspondingly matched to the measured pressure in the clinic setting. The in vivo application of a matched pressure improves surgical outcome by avoiding recurrent incontinence or material degradation from unduly high applied tension. The device in the clinic may have a different structure than the one used surgically. For example, the different structure may relate to how and what surface the pressure sensor is connected. In the clinic, it may be applied to a glove outer surface, a finger within the glove, or a glove inner surface, positioned between the finger exerting the force and the corresponding patient surface. The device in surgery, in contrast, is positioned between the patient tissue surface and the medical device (e.g., not the finger) that is to exert the force on the tissue.

In an embodiment, the method is for measuring the pressure generated on the urethra by an external force. The external force may be generated directly by a medical provider and/or by a material surgically inserted by a medical provider, such as a sling or mesh sling.

In another embodiment, the method is for treatment of urinary stress incontinence of a patient. In an aspect, the patient is a female. In an aspect, the patient is a male. A pressure sensor system is introduced adjacent to the urethra of the patient in a clinical setting. The sensor may be affixed at an appropriate position, such as by medical tape. An application pressure is applied against the urethra, such as an application pressure that is sufficient to temporarily alleviate a urinary stress incontinence symptom. In this aspect the pressure sensor is positioned between the application pressure and the urethra, so that the actual application pressure is quantified via the output from a pressure sensor of the pressure sensor system. Accordingly, an alleviation output from the pressure sensor is identified as corresponding to a minimum pressure sufficient to alleviate the urinary stress incontinence symptom. The alleviation output value is noted and used during the subsequent surgical procedure.

Alternatively, the pressure sensor system is affixed to the surface of a glove worn by the person exerting the application pressure. The affixation may be either internal or external relative to the glove surface. The sensor is positioned between the force-applying surface (e.g., a finger-tip) and the surface upon which the force is applied (e.g., a biological surface such as the urethra). The sensor is operably connected to a display that provides a read-out from the pressure sensor, such as a numeric read-out of an average pressure or force detected by the sensor, or a voltage output that is related thereto. In this manner, precise and real-time pressure exerted by a person against a surface is known. The sensor may be hard-wired to the display. Alternatively, the sensor may be connected to the display through wireless means, such as radio frequency. In an aspect where a single pressure sensor is used, the display is of one pressure sensor. In an aspect where the user exerts a force on a surface using multiple contact points, such as multiple fingers, the display can simultaneously display the numerical output from each of the pressure sensors. Alternatively, the display may be a graphical representation of the applied force, such as by a color map with different colors representing different applied force or pressure.

The pressure sensor is capable of connecting to other surfaces, besides a glove. For example, one or more pressure sensors may be connected to a sterile cover or blanket used to determine pressure in a wide range of medical applications. For example, anesthetized, or otherwise unconscious or uncommunicative patients cannot warn medical personnel about uncomfortable pressure points that may have a deleterious effect on the body. Accordingly, the devices and methods provided herein are compatible for use in other applications, including "passive" applications where the patient is the person responsible for the force that is being monitored in real-time. Above a certain threshold level, the device may alarm to indicate to medical personal that corrective action should be taken. This can be of particular use in a rehabilitation setting, where the patient may be confined to bed for relatively long periods of time, and such a pressure sensor system and method used to minimize risk of bed sores. In another aspect, the sensor may be an implantable surface affixed to a surface of a medical device that is implanted into a patient. In this aspect, the sensor may remain in the patient along with the implanted device.

A support material, such as a surgical sling (or "mesh sling") is inserted in the patient to support the urethra. The pressure sensor of the pressure sensor system is positioned to determine the pressure exerted by the sling on the urethra. For example, the pressure sensor may be positioned between the sling and the urethra, so that any pressure exerted by the sling on the urethra is accurately detected by the sensor. A pressure is exerted on the urethra by generating a force on the surgical sling (e.g., adjusting the tension on either end of the sling adjacent to the contact points between the sling and urethra), wherein the exerted pressure is detected by the pressure sensor. The optimal generated force on the surgical sling is selected by comparing the exerted pressure to an alleviation output that was clinically determined. In an aspect, the optimal generated force substantially corresponds to the alleviation output of the identifying step, thereby treating urinary stress incontinence of the patient. The term "substantially corresponds" is used with the understanding that the optimal generated force need not be exactly identical to the alleviation output in order to achieve significant benefit. Instead, there is a certain degree of tolerance. In an aspect, substantially corresponds refers to an applied pressure that is within about 20% of the alleviation output.

In an aspect where the pressure sensor is positioned between the support sling and the urethra on which the sling exerts pressure that is detected by the pressure sensor, any of the methods provided herein further comprise the step of removing the sensor from between the sling and the urethra once the appropriate pressure has been applied to the urethra by the sling, including by a sliding removal action. In an embodiment, the fastening means is removed to facilitate removal by sliding, such as be removing the adhesive tape or fasteners that secure the pressure sensor to the sling. Alternatively, the pressure sensor is affixed to the sling, and the fastening means connects the pressure sensor to the sling. The fastening means can then be removed and risk of unwanted irritation or damage to the biologic surface minimized. In an aspect, the pressure/force sensor portion is thin, such as less than or equal to 1 mm, less than or equal than 0.5 mm, or selected from a range that is between about 0.15 mm and 0.35 mm.

In another embodiment, the invention is a method of assessing real-time pressure exerted against a biological surface for a desired application force. This is particularly useful for medical caregivers applying forces to a patient, either directly by the caregiver or through a medical device, such as an implantable medical device. A pressure system is introduced adjacent to the biological surface and an application force applied onto the biological surface. A pressure sensor output is identified in real-time from the pressure sensor for the applied application force. In this manner, the pressure (or force) exerted against the biological surface is identified in real-time.

In an aspect, the application force is generated by a finger or hand of a person, such as a medical caregiver. Alternatively, the application force is instead generated by the biological surface, such as by a patient supported by supporting surface. In another embodiment, the force is generated by a medical device, such as an orthopedic device or a support sling to treat urinary stress incontinence system.

In an embodiment, the surface is the surface of the urethra of a patient, or another tissue such as bone or skin. In an aspect the biological surface is in a living human.

In an aspect, wherein the application force is sufficient to temporarily alleviate a urinary stress incontinence symptom. For example, in a non-surgical setting, the external force or pressure applied to the urethra sufficient to alleviate urinary stress incontinence is identified in real-time. The method optionally further includes in a surgical setting inserting a surgical sling to support the urethra and positioning the pressure sensor system to determine a pressure exerted by the surgical sling on the urethra. A pressure is exerted on the urethra by generating a force on the surgical sling, wherein the exerted pressure is detected (in real-time) by the pressure sensor. This real-time exerted pressure on the urethra is adjusted (e.g., by adjusting the sling tension) so that the urethral pressure sensor output substantially corresponds to the application force sufficient to temporarily alleviate a urinary stress incontinence symptom determined in the non-surgical setting. In an aspect, substantially corresponds refers to an urethral pressure sensor output that deviates by less than or equal to 20% of the application force pressure sensor output that alleviates at least temporarily an urinary stress incontinence symptom.

In another embodiment, the invention is a device, such as a device for implementing any one or more of the methods disclosed herein. In an aspect the device is for measuring urethral pressure, such as urethral pressure pre- or post-operatively or during surgery for patients suffering urinary incontinence. A pressure sensor is adapted for operable connection to a patient's urethra.

In another embodiment, the device comprises a pressure sensor portion operably connected to a microcontroller and a display for real-time display of a pressure output by the pressure sensor and microcontroller. In an aspect, the display is a numerical display that a surgeon or medical caregiver can easily see and understand, and take action as appropriate. This is particularly suitable to applications where the medical caregiver is the person responsible for generating the force or pressure being measured. In an aspect, the pressure sensor is affixed to a glove, such as a glove finger surface that corresponds to the finger-tip of the medical caregiver used to exert a force against a surface. In another embodiment, the device comprises a pressure sensor portion affixed to a sterile cover. Any of the devices provided herein are optionally connected to a display to provide a real-time read out from the pressure sensor, such as a numerical read out of an average applied force or pressure, that is conveniently displayed to the medical caregiver. This provides the capacity for real-time force or pressure adjustment, with the force or pressure reliably detected and displayed.

The sensors are operably connected to a microcontroller that provides necessary processes to provide a usable output from the pressure sensor. For example, the output from the microcontroller may be fed to a display to provide real-time output of the pressure, including by a wireless connection. In another example, the microcontroller can store a time course of the pressure from the pressure sensor, including a time course of a pressure map from a plurality of pressure sensors so as to provide longitudinal variations in the applied pressure. In an embodiment, the microcontroller is self-contained and functionally portable. The device, and related methods, can use any number of sensors as desired. There is, however, a generally practical upper-limit to the number of sensors required to accurately measure the map because there are certain relevant positions along the urethra. These positions are over, for example, constricted portions of the urethra that is functionally attributed to urinary incontinence. Accordingly, as the number of sensors increase, redundant and unnecessary measurements will be obtained. Accordingly, in an aspect, the plurality number is less than or equal to 16, less than or equal to 8, or is 6 or 4 sensors. In an aspect, a single pressure sensor is used. In an embodiment, the microcontroller is connected to the sensor or to each of the plurality of pressure sensors by a signal-conducting wire. In an aspect, the communication between any portions of the device is wireless. For example, the pressure sensor output may be wirelessly communicated to the microcontroller and/or wirelessly communicated to the display.

Although specific exemplifications herein relate to a urinary incontinence setting, the devices and methods provided herein are useful in a variety of applications where it is desired to measure the pressure exerted on, or exerted by, a material. In an aspect, the pressure sensor portion may be affixed to the object that applies a force onto the material. In one embodiment, the sensor may be place on an individual's fingertip, or a glove's finger surface. In this manner, concerns related to proper pressure sensor affixation to a material surface (and corresponding removal of the affixation means) is avoided.

In an aspect, any of the methods provided herein are directed to a method to obtain data, such as the pressure exerted against a surface, including a surface that is biological in nature. In this aspect, the technique of applying the pressure sensor against a biological surface such as for the urethra surface may be considered a minor intervention, involving a safe, routine technique of application of a surface pressure over a patient region corresponding to the urethra, with a pressure sensor to measure the applied pressure. Accordingly, for any of the methods provided herein that recite a surgical treatment step, the surgical treatment step is optionally disclaimed, including in jurisdictions that consider such surgical treatment steps to be prohibited patentable subject matter.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION OF THE INVENTION

Figure 1:
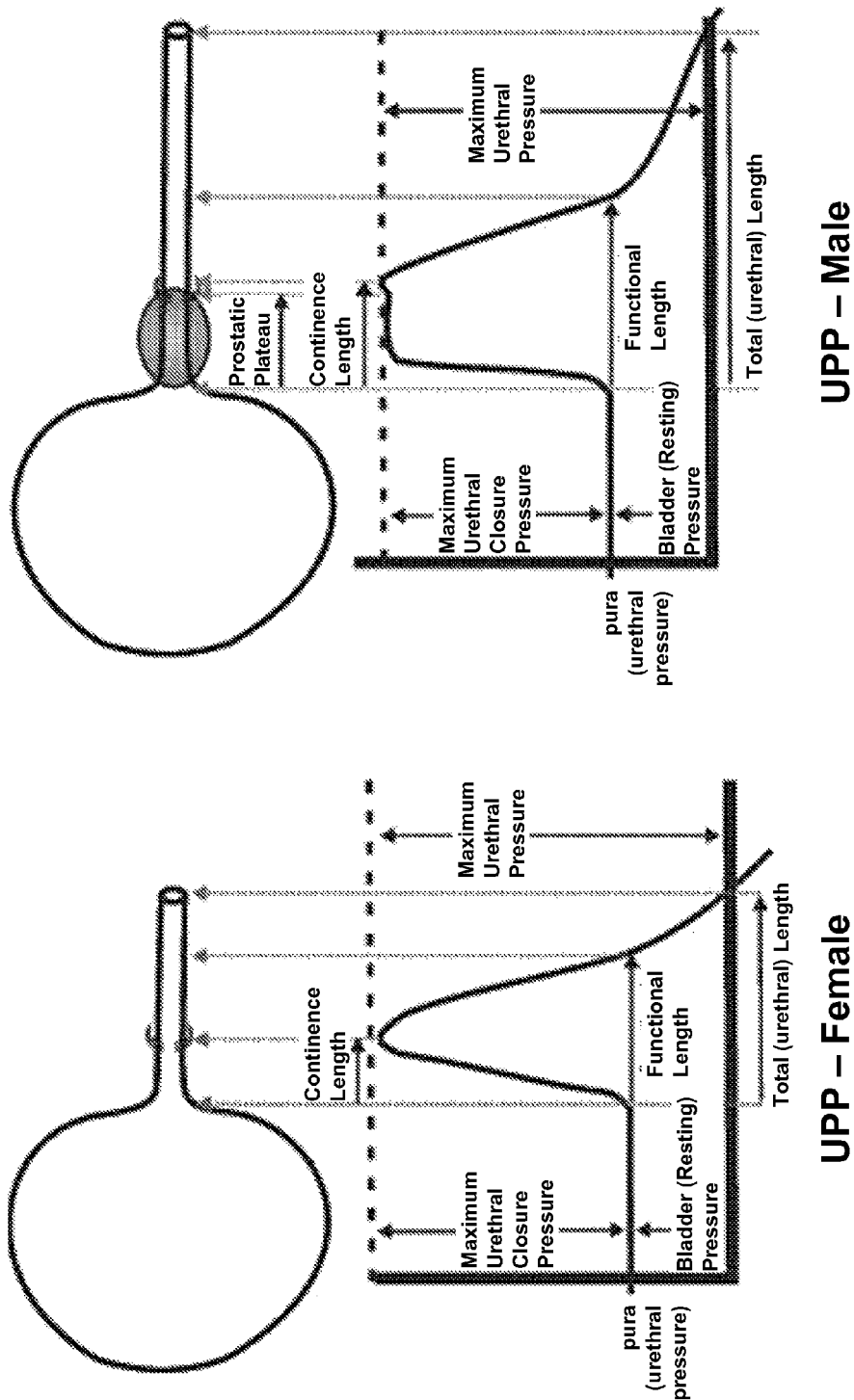
FIG. 1 is a graphical representation of the urethral pressure profile (UPP) along a path from the bladder and along the urethra.

"Output" refers to a signal that is generated by a sensor operably connected to a surface, such as the urethra or the region surrounding the urethra. Generally, the signal is an output voltage from a pressure or force sensor, whose voltage magnitude is dependent on the force applied to the sensor. "Connected" refers to a sensor that is reliably positioned in a specific location relative to the surface, such as the urethra, so that a pressure exerted on the surface, including the urethra (either externally (e.g., extra-luminal) applied or internally (intra-luminal) applied) is detected and reliably measured by the sensor. The sensors are secured to specific regions of interest of the surface or the urethra, including directly above the urethra. Any means of connecting the sensor to the user may be used, including by underlying adhesives and/or overlying tape, dressing or bandage that facilitates temporary affixation. In an embodiment, a Tegaderm™ dressing may be used to reliably position and affix the sensor. Medical tape may also be used. So long as the affixation provides reliable positioning in that the sensors do not migrate during use and are not excessively padded (thereby causing an under-recording by the pressure sensor), any kind of affixation material may be used. The sensors may be applied in a clinical setting, such as over the skin, or during surgery (e.g., adjacent to the urethra and underneath the skin).

"Stress incontinence symptom" refers to a measurable or observable physiological parameter associated with urinary stress incontinence. One example of a stress incontinence symptom is involuntary urinary leakage.

"Clinical setting" refers to pre-operative conditions, wherein there has not been any surgical intervention or any procedure that is invasive to the body.

"Pressure map" refers to the use of two or more sensors to provide a simultaneous measure of pressure over a surface, such as in the urethral region or along the urethra at distinct locations simultaneously. A pressure map is useful in providing a more refined and detailed real-time measure of pressure distribution over a surface, such as along the urethra, thereby providing improved surgical outcome for urinary stress incontinence intervention. In an aspect, the display displays a numerical value such as a pressure or other output from which pressure is calculated or related. Similarly, the display may display a map of pressure values over the surface for embodiments where more than one pressure sensor is used.

"Operably connected" refers to a configuration of elements such as between device components or between a tissue and a device component, wherein an action or reaction of one element affects another element, but in a manner that preserves each element's functionality. Operably connected device components may be in contact, such as in electrical contact by a signal-conducting wire between a sensor and a microcontroller containing a microprocessor. Alternatively, operably connected components may be connected by one or more intervening components. In another alternative, operably connected components may not be physically connected, but may be wirelessly connected such that a signal is output from one component and wirelessly received by a second component. In an embodiment, a force or pressure may be applied to a surface, such as a force or pressure on a tissue such as the urethra, and a pressure sensor is said to be operably connected to the tissue such as the urethra when the pressure sensor provides a reliable and repeatable output that is dependent on the applied force. Accordingly, in an aspect, a pressure sensor that is "adjacent" to the urethra is said to be "operably connected" or "in operable connection" with the urethra. In this aspect, adjacent may refer to a configuration where there is direct physical contact or a configuration where intervening tissue separates the pressure sensor from the urethra.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

FIG. 1 summarizes the pressure distribution along a path from the bladder through the urethra in a female (left panel) and a male (right panel). Each incontinent patient, however, has a specific pressure point positioned under the mid urethra, wherein for an applied pressure magnitude at that position, continence mechanisms are restored. Accordingly, in an aspect, the pressure is applied at a position that generally corresponds to the maximum urethral pressure of the UPP profile. In an aspect, the position corresponds to the portion of the urethra labeled "functional length" in FIG. 1.

Figure 2:
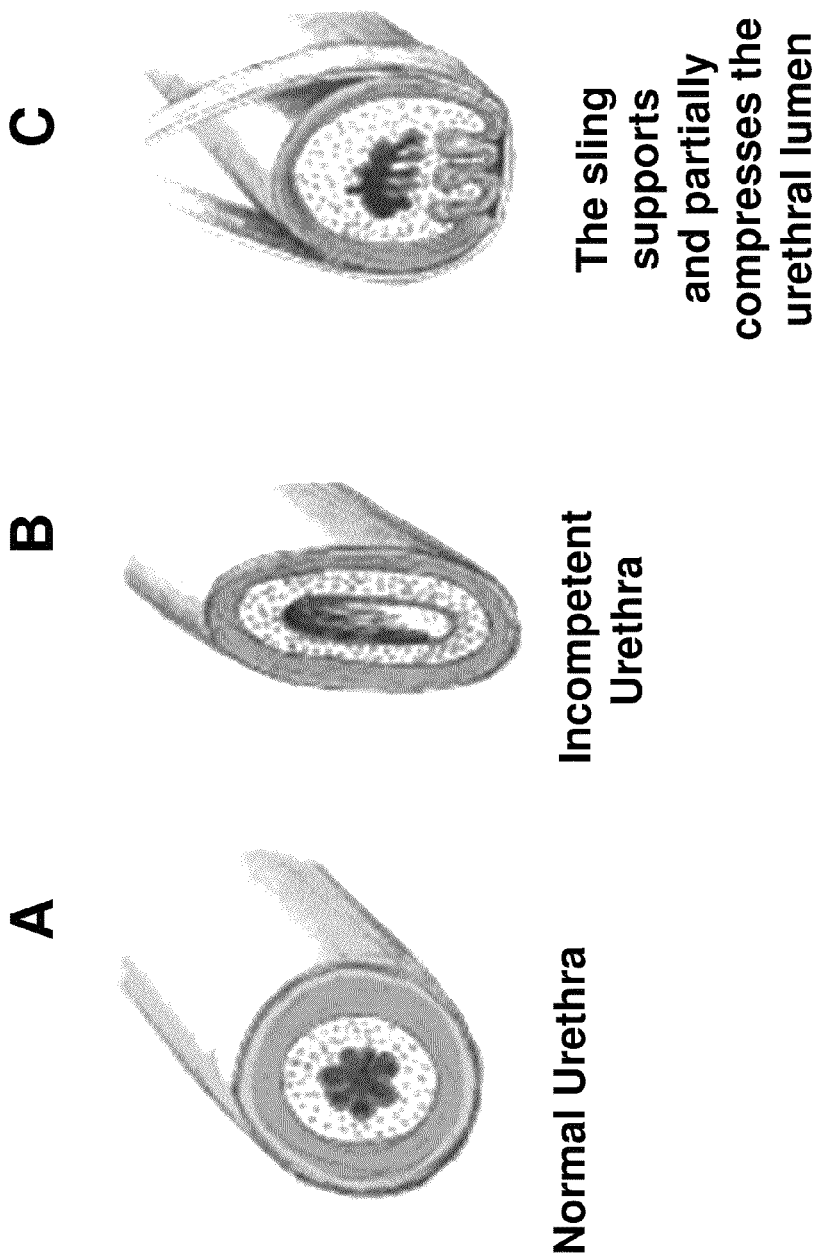
FIG. 2 is a schematic illustration of a urethra showing: A. a normal urethra; B. an incompetent urethra; and C. a surgical intervention to correct the incompetent urethra by a sling that supports and/or partially compresses the urethral lumen.
Figure 3A:
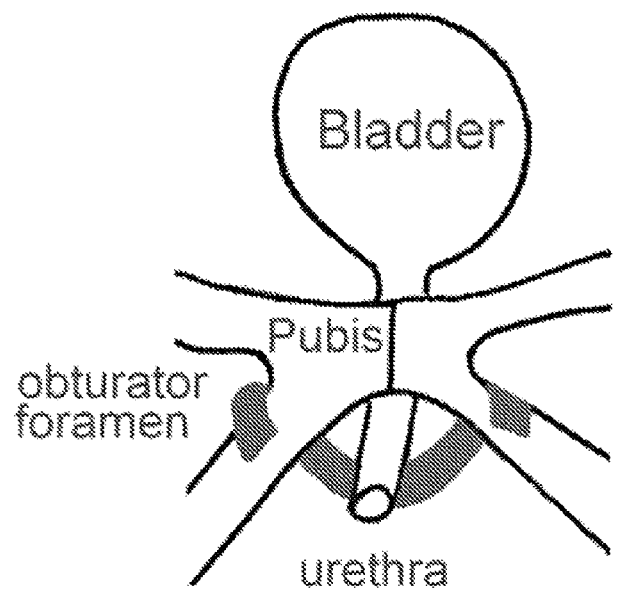
FIG. 3A is a schematic illustration of positioning of a sling to support the urethral lumen, thereby alleviating stress incontinence. 3B illustrates the use of a pressure sensor to provide real-time display of the pressure exerted against the urethra by the sling support.

FIG. 2 illustrates the structural differences between a normal urethra (A) and an incompetent urethra (B). An incompetent urethra generally has a misshapen lumen resulting in stress incontinence. One procedure for curing, or at least alleviating, the symptoms related to stress incontinence is by introduction of a material to support and partially compress the urethral lumen. As shown in FIG. 2C, the material may correspond to a sling, including a transobturator (TOT) sling or mesh sling. FIG. 3A shows how the sling 30 may be connected in vivo to provide support to the urethra 40. One drawback of this procedure, however, relates to determining whether an appropriate force or pressure is exerted on the urethra. If the applied pressure is too low recurrent stress incontinence may occur. If the pressure is too high, infection and erosion of the applied material becomes problematic. Accordingly, provided herein are devices and methods that reliably and accurately determine a minimum pressure required to alleviate incontinence and ensure that minimum pressure is surgically achieved.

Example 1

Device and Method Characterization

Figure 3B:
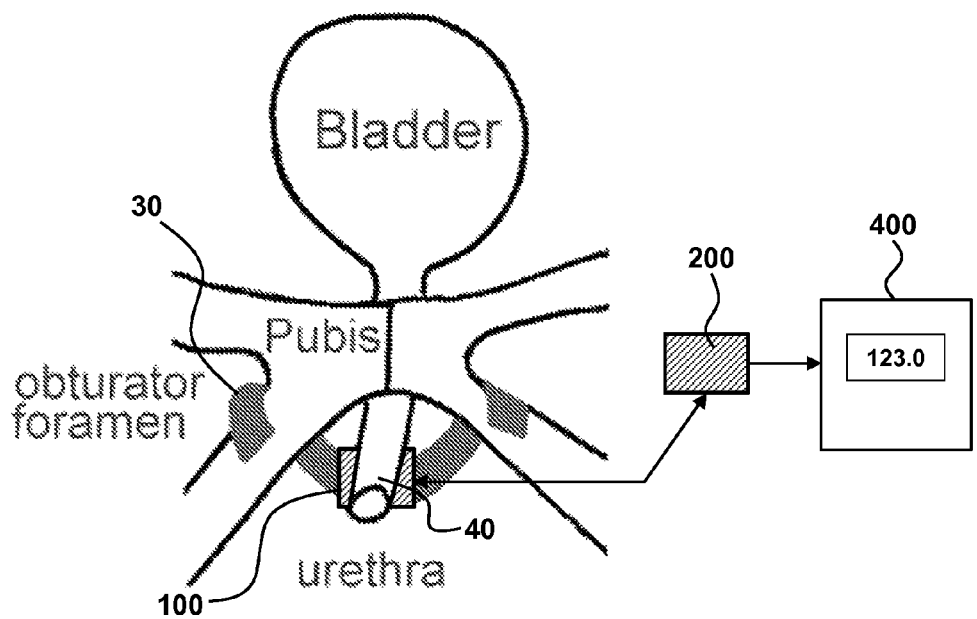

FIG. 3B illustrates placement of pressure sensor 100 between the sling 30 and urethra 40, along with the microcontroller 200 and display 400. Appropriate pressure or force generation on the urethra by the surgical intervention provides improved surgical outcome and reduces post-surgical complications. In this manner, real-time readout 400 of the pressure or force used to support the urethra is provided, thereby providing precise adjustment of sling 30 to obtain the desired supporting pressure or force on the urethra. In an aspect, the desired pressure is obtained presurgically (alleviation output), and is matched during surgery by varying the tension of the sling 30 to generate a pressure readout 400 that corresponds to the desired pressure (alleviation output).

The pressure sensor system 10 provided herein may have one or more pressure sensors and a drive circuit to accommodate the one or more sensors. In an aspect, the device comprises one pressure sensor. In an aspect, the device may accommodate up to eight sensors, such as a device having a pressure sensor number selected from a range that is greater than or equal to 1 and less than or equal to 8. A microcontroller receives analog inputs from the sensors and converts them to digital signals. The digital signals may be immediately displayed. In an aspect where the device is used in a surgical procedure, a surgeon may, in real-time, determine the appropriate positioning and force on the urethra to ensure optimal pressure generation on the urethra to alleviate incontinence. Optionally, the digital signals are stored and the data retrieved from the microcontroller, such as by a File Transfer Protocol (FTP) server, as desired.

Figure 4:
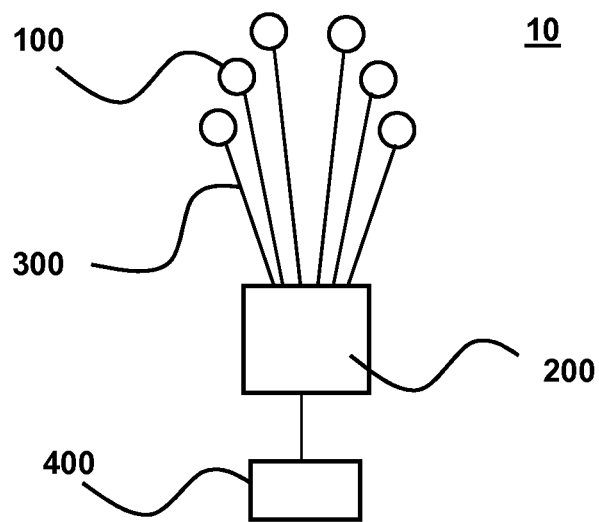
FIG. 4 is a schematic illustration of a device for measuring pressure exerted against a surface.

Referring to FIG. 4, provided herein is a device 10 formed from a plurality of pressure sensors 100 and a microcontroller 200. The microcontroller is optionally self-contained and sufficiently small to be portable and placed, for example, wherever desired. The pressure sensors 100 are operably connected to the microcontroller. FIG. 4 illustrates an embodiment where the connection is via signal-conducting wires 300, such as a wire that transmits a voltage output from the pressure sensor 100 to the microcontroller 200. Another example of an operable connection is via a wireless connection between sensor 100 and microcontroller 200. The pressure sensors may be displayed in real-time by a computer/display 400 positioned in the surgeon's field of view during a medical procedure.

The microcontroller 200 contains a chip with memory storage capability for storing a time-course output from pressure sensors 100. Alternatively, the microcontroller may transmit the output to a remote location where the data is stored, observed, and/or analyzed. The observation may be in real-time, such as by wireless communication to a display component (e.g., a monitor), thereby providing instant readout of the pressure exerted against a surface. In an aspect, the device may provide both storage and real-time display to facilitate instantaneous evaluation of pressure and later analysis. In an embodiment, the microcontroller chip is an RCM4000 RabbitCore® microprocessor (see, e.g., www.rabbit.com/products/rcm/4000/) that receives analog input from the sensors and converts them into digital signals to be stored in its memory.

Figure 5:
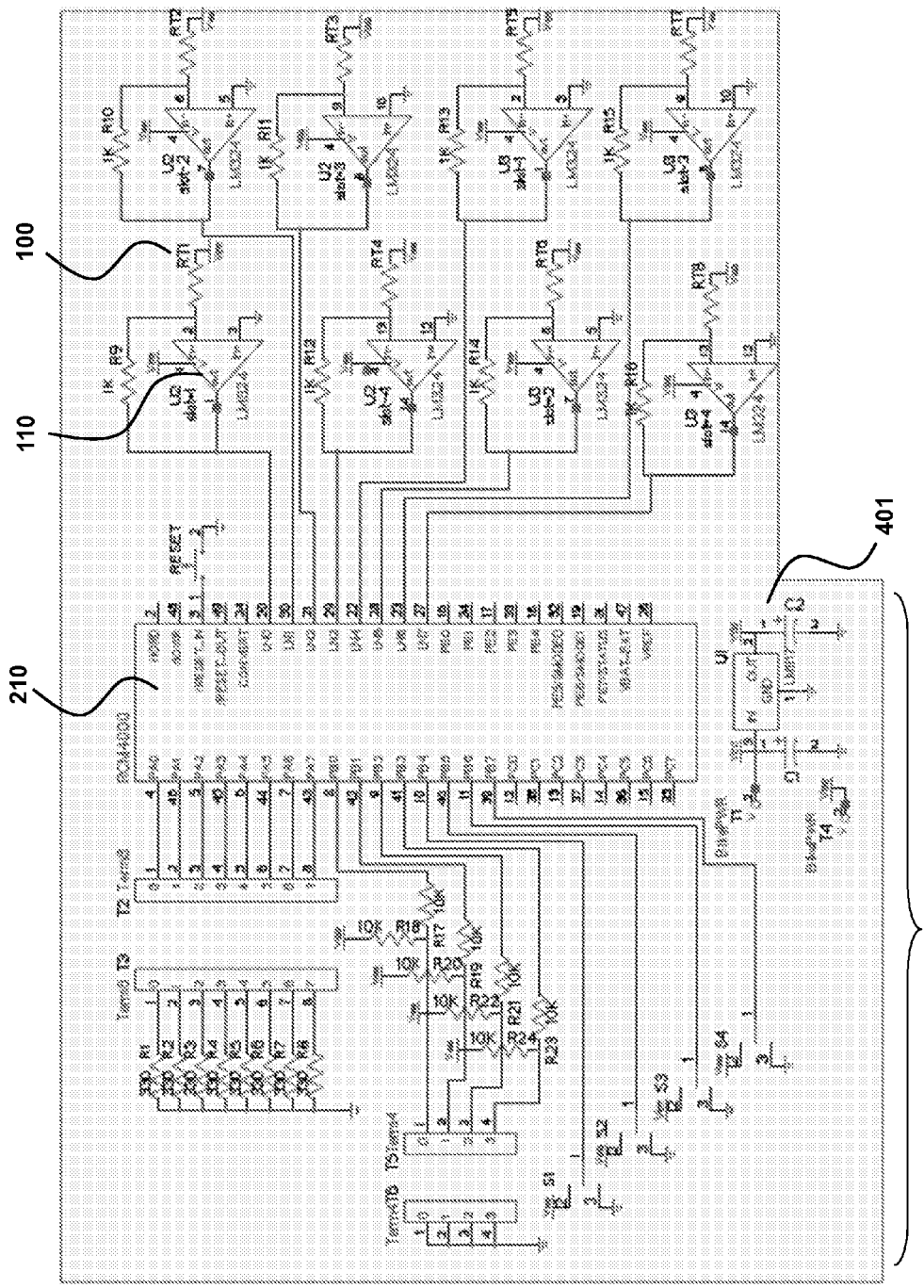
FIG. 5 is an electrical circuit for one embodiment of a device for measuring pressure exerted against a surface, including a urethral pressure monitor.
Figure 10:
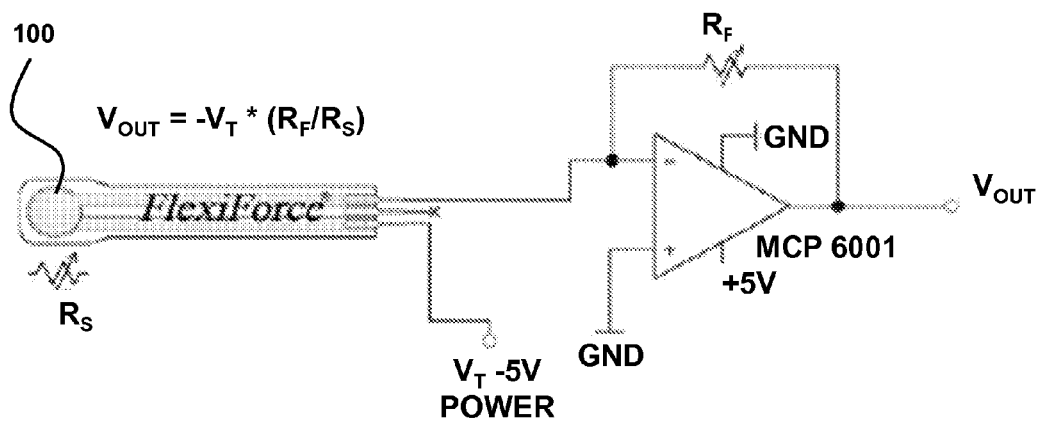
FIG. 10 is a representative electrical circuit for measuring pressure exerted against a surface by a pressure sensor, including a FlexiForce® sensor.

FIG. 5 is an electrical circuit diagram of one embodiment of the device. The sensors 100 are electrically connected to a microprocessor 210 confined in microcontroller 200 portion such as via individual operational amplifiers 110. A close-up view of the operational amplifier-pressure sensor portion is provided in FIG. 10. Referring to FIG. 10, desirably the supply voltages (e.g., $V_T$) are constant; the reference resistance ($R_F$) is 1 k$\Omega \leq R_F \leq$ 100 k$\Omega$; the pressure sensor resistance $R_S$ at no load is greater than 5M$\Omega$; and the maximum current is about 2.5 mA. Other optional components are included in the microcontroller as desired, including switches and LED to indicate sensor and/or recording status. In this example the operational amplifiers are National Semiconductor LM324 low power quad operational amplifiers. The device may be powered by a power source 401 (see FIG. 5), such as a battery for portable use or connected to a stationary source (e.g., wall outlet or power grid) for use in controlled environment (e.g., in a clinical or surgical setting with a stationary patient). To enhance portability, the eight individual op-amps can be replaced with two low power quad op-amps. This has an advantage of decreasing the power requirements, dimensions, and the weight of the device. In an embodiment, the pressure sensor output is displayed in real-time. Accordingly, in an embodiment the microcontroller need not store the sensor output. In an embodiment, the sensor output may be directly fed for display. In an embodiment where one pressure sensor is used, only one op-amp 110 is required.

Figure 6:
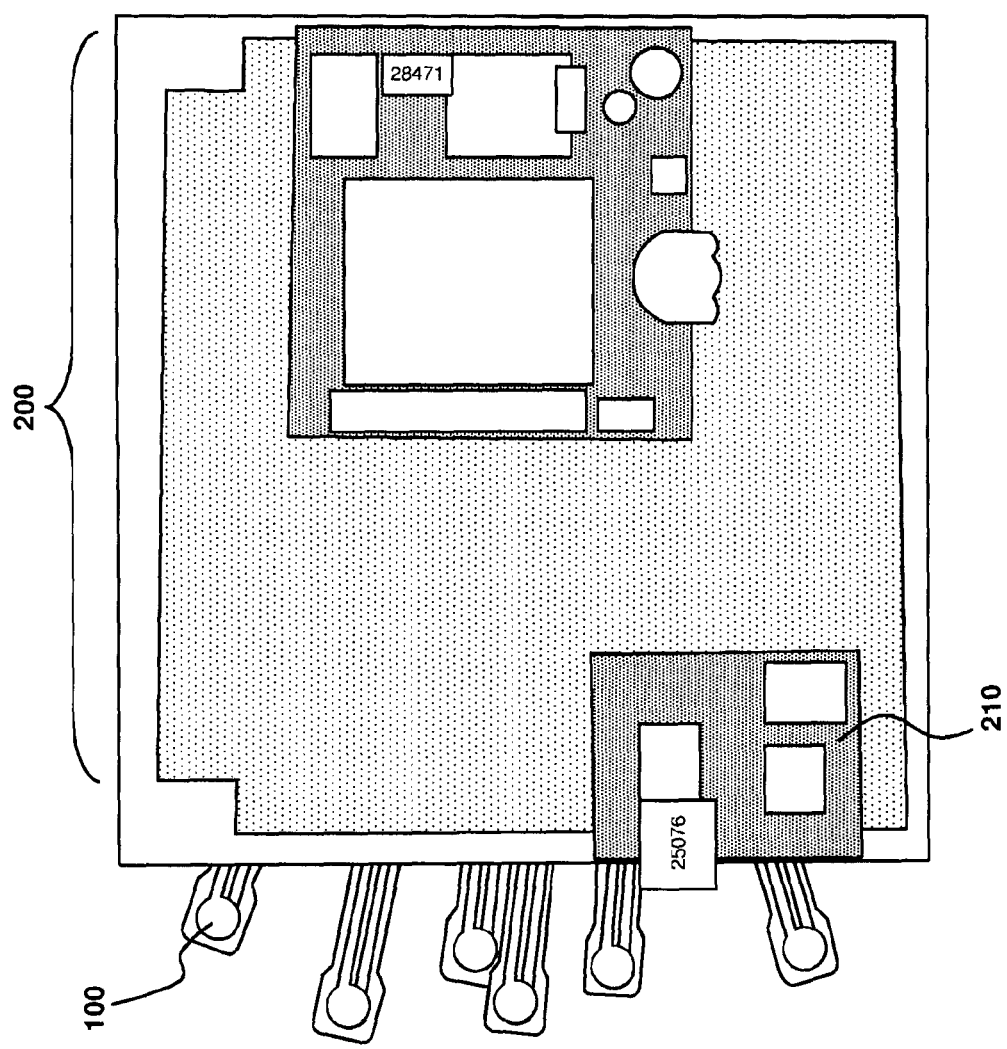
FIG. 6 is a line drawing schematic illustration of one embodiment of a pressure measuring device.

FIG. 6 is a line drawing schematic illustration of a device. The RCM4000 microprocessor 210 is embedded in a motherboard and a plurality of sensors 100, are operably connected thereto, such as via electrical connections to the motherboard to which the microprocessor is connected. Any sensor known in the art may be used so long as the sensor is capable of reliably providing a time course of force or pressure exerted against a surface. For example, the sensor may be a transducer, including a pressure or a force transducer. As used herein, force transducer and pressure transducer are used interchangeably as the measure of one parameter may be used to calculate the other parameter by the formula P=F/A, where P is pressure, F is force, and A is the area over which the force is applied. Examples include sensors having a resistive or capacitive element that changes under an applied force or pressure, so that a change in an electrical parameter corresponds to a change in applied force or pressure. One example of a suitable sensor is a Flexiforce® force sensor from Tekscan (South Boston, Mass.) (see, e.g., U.S. Pat. No. 6,272,936). Any sensor, however, that is thin so as to provide non-intrusive measurement and capable of reliable positioning to a confined region as desired depending on the application (e.g., urethra for urinary stress incontinence; perineum region for seat design and testing) may be used. In an aspect, the sensor measures the force over an area that is circular having a diameter that is less than or equal to 1 cm, 0.8 cm, 0.6 cm or about 0.95 cm (0.375"). In an aspect, the maximum dimension of the sensor is selected from a range that is greater than or equal to 5 mm and less than or equal to 10 mm.

Figure 7:
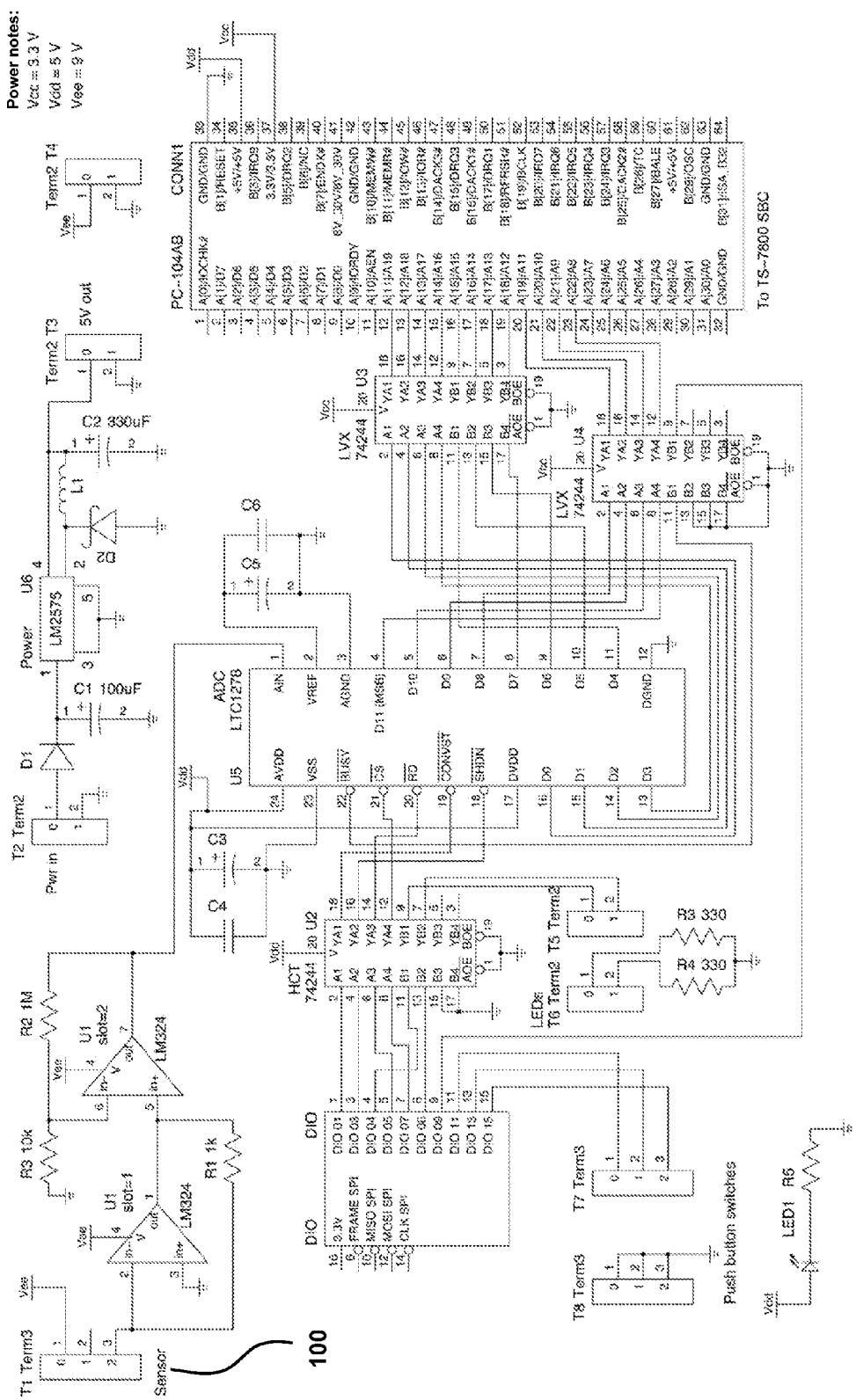
FIG. 7 is a circuit diagram schematic of a pressure measuring device suitable for connection to a glove.

FIG. 7 is another example of a circuit diagram that is particularly suited for sensing and displaying force application in the about five pound range. In this embodiment, output from sensor 100 is connected to two op-amps (a non-inverting and inverting) in series fed to a microcontroller and display for real-time display. Depending on the sensor specifications and desired pressure or force application detecting range, resistors R1, R2 and R3 are selected. The output from the op-amps is fed into an analog-to-digital converter (ADC) and to a system component, such as a PC-104 system component for display of the pressure or force detected by sensor 100, or an electric parameter related thereto.

The sensor may be incorporated into a force-to-voltage circuit as shown in FIGS. 5-7 and 10. The device shown in FIG. 6 has a final dimension of 9×9×4.5 cm with a total mass of 200 grams and, with the components exemplified therein, pressures from six distinct locations can be displayed or stored for up to four hours. The portability of the device allows placement of the microcontroller portion anywhere desired, thereby avoiding interference with any desired clinical or surgical procedure.

Figure 8:
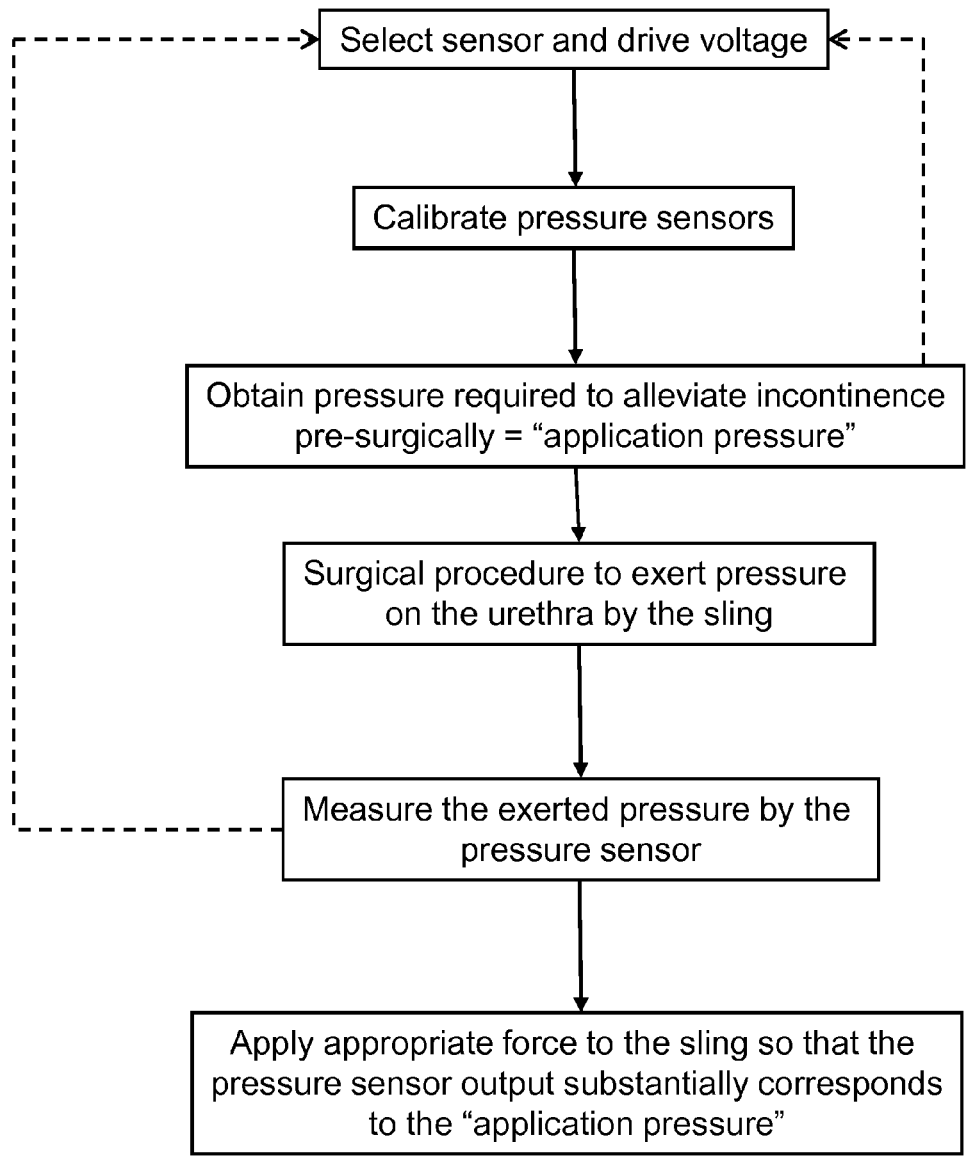
FIG. 8 is a flow-diagram of a methodology for using a pressure sensing device to alleviate stress incontinence.

FIG. 8 summarizes various aspects related to use of the device to quantify pressure or force exerted against the urethra during incontinence treatment. As a preliminary step, various device parameters may be selected so as to maximize the sensitivity of the device to typically encountered forces, such as by selection of sensor sensitivity range. Different applications may have different relevant forces. For example, pressure sensors and/or drive voltages are selected to provide desired force-range sensitivity. In an aspect where the application is urinary incontinence treatment, typical forces may be about up to 5 pounds. A pressure sensor having a suitable sensitivity range is then selected, such as a maximum sensitivity that is about two times the typically encountered maximum force. With an appropriate driving and control circuit, pressure sensors may be tailored to provide sensitivity over a desired range by appropriate selection of an input parameter, such as the driving voltage ($V_T$) and/or reference resistance $R_F$ (see FIG. 9). In this manner, good sensitivity over a desired pressure or force range is achieved. For example, a sensor having a force sensitivity over a range of 0 to 1 pound is used to measure an applied force that is about 5 pounds by changing the drive voltage of the circuit that powers the sensor to increase the 0 to 1 pound sensor range to a 0 to 10 pound range. In this manner, the pressure sensor device is "matched" to the force applied during pressure sensor use. This step is summarized in FIG. 8 by the "select sensor and/or drive voltage" step, and can be informed by the "application pressure step" and/or the measured pressure during the surgical procedure as indicated by the dashed feedback arrows to match and maximize device sensitivity to a particular application or device use. In an aspect, the sensor sensitivity is selected for a range that is up to about 10 pounds of applied force, or up to about 5 pounds of applied force.

Figure 9:
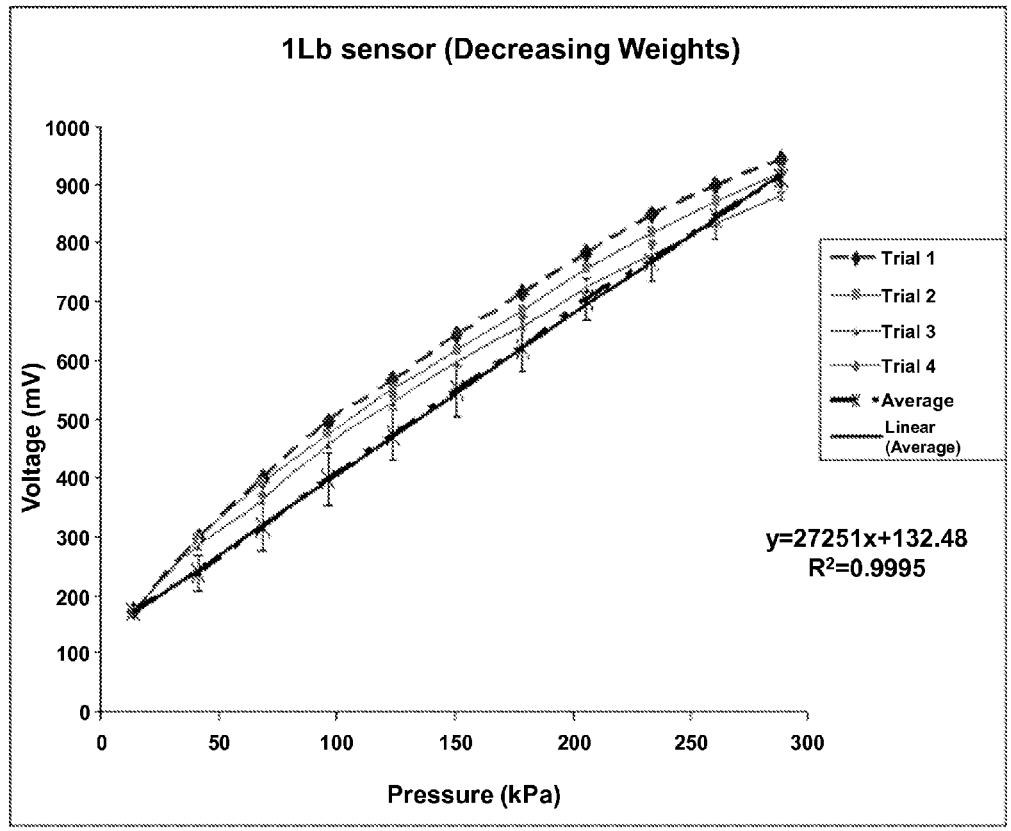
FIG. 9 is a sensor calibration curve of the sensor output (mV) as a function of different applied pressures (kPa).

As a preliminary step, the sensor is calibrated so that an output from the sensor corresponds to a force or pressure, as desired. There are many types of calibration procedures for generating a calibration curve so that a pressure may be calculated for a given sensor output, such as voltage. For example, a sensor may be connected (e.g., taped) to the center of a syringe plunger orifice. A force is applied by placing a known weight directly to the top of the syringe stopper. Because both the orifice cross-sectional area and the applied force (from the weight) are known variables, the pressure exerted on the sensor is known. The voltage output from the sensor is obtained, such as a mean of several separate measurements, for a given applied pressure. The pressure is varied by applying different weights so that a pressure versus output voltage calibration curve is obtained. FIG. 9 is an example of a pressure calibration curve for a device that uses a 0 to 1 pound Flexiforce® (Tekscan, South Boston, Mass.) sensor. The curve is generated from multiple trials where a known weight is applied to the sensor, over a range between about 0 kPa and 300 kPa. In this manner, pressure is determined as a function of output voltage from the circuit. In an aspect the calibration curve is linear. In an aspect the calibration curve is non-linear. In an aspect the calibration curve has linear portions and non-linear portions.

To assist in the treatment of incontinence, the pressure required to alleviate incontinence is determine before surgery (e.g., "clinically"). In this aspect, the minimal pressure on the urethra required to stop urine leak before surgery is determined by applying various forces to the urethra with the pressure sensor positioned between the applied force and the underlying urethra. In this manner, the required pressure (or "application pressure") is empirically determined for an individual patient. This minimum pressure is referred to as the "application pressure" with a corresponding "alleviation output" from the device for that measures that application pressure. With the application pressure known, the surgical procedure may commence. In an aspect the surgical procedure relates to use of a TOT (transobturator) sling to exert sufficient pressure on the urethra to alleviate incontinence (with the effect diagrammatically illustrated in FIG. 2 (compare 2B with 2C). Appropriate force from the sling on the urethra is ensured by positioning the sensor relative to the sling and urethra so that the pressure exerted by the sling is measured by the pressure sensor. In an aspect, the sensor is positioned to correspond to the contact point between the sling and the urethral vessel (FIG. 3B). Tension in the sling is then adjusted, as well as positioning of the sling along the urethra, to ensure the exerted pressure either substantially corresponds to the application pressure, is functionally equivalent to the application pressure, or is equal to the application pressure. Once the appropriate tension in the sling is achieved (e.g., to provide a pressure sensor output that substantially corresponds to the application pressure), the sensor is removed. Accordingly, the sensor is appropriately thin so that it can be slid out from between the sling and the urethra.

Example 2

Clinical Use

The device is optionally used in clinical and/or surgical procedures. Specifically, the minimum pressure required to prevent leaks are determined in a male and a female patient and intraoperative measures are obtained. Alternatively, the device is used for a non-surgical procedure.

Table 1 provides a summary of use of the device with six patients suffering urinary stress incontinence (3 male and 3 female). In a clinical setting, the pressure sensor device was used to quantify the amount of force required to stop leakage (as reflected in the last column "stop leakage measure"). Various other relevant parameters are summarized in the table. With this information, a sling is implanted with a generated pressure or force on the urethra measured by a pressure sensor that is equal to or substantially corresponds to the stop leakage measure obtained in the clinical setting. This process of measuring the pressure in the clinic provides a suitable range of pressures that can be useful in a subsequent surgical-intervention. For example, the desired pressure range corresponds to a minimum pressure necessary to stop leakage and a maximum pressure that results in stop flow. Accordingly, during surgery, the sling supporting the urethra is adjusted to provide a tension that is greater than or equal to the minimum pressure (e.g., to stop leakage) but that is less than the maximum pressure (e.g., so that flow is not completely stopped). A sling that provides such a pressure on the urethra should lower complication risk and provide a higher success rate than procedures that do not measure pressure and match it to the clinically-determined pressure range.

Example 3

Pressure Sensor Incorporated into a Glove for Medical Procedures

Figure 11:
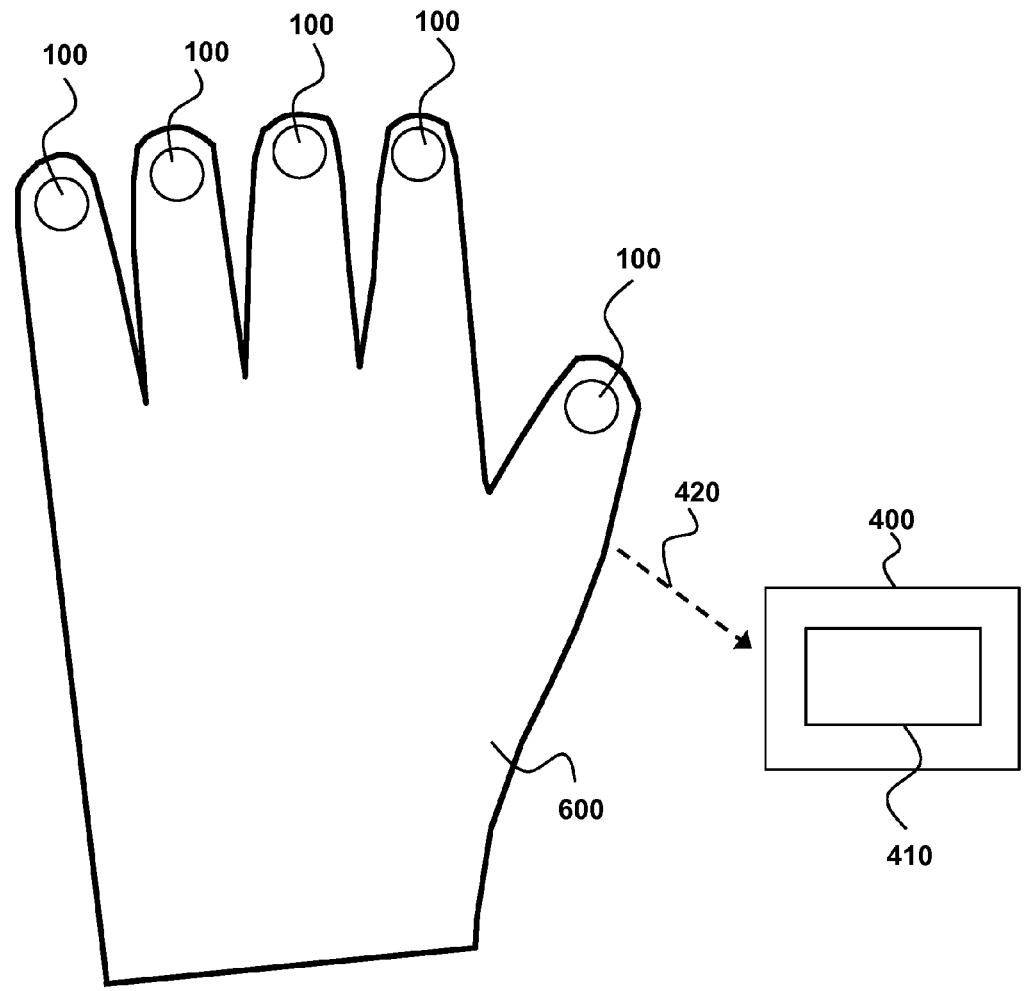
FIG. 11 is a schematic of a pressure sensor device connected to a surgical or sterile glove used in medical applications.

The pressure sensor device and system is useful for a number of applications. For example, FIG. 11 illustrates pressure sensor(s) 100 connected to the fingertip of a glove 600. The sensor(s) 100 can be connected to an inner or to an outer surface of the glove. In an aspect, a single sensor is connected to the glove, such as at a glove fingertip corresponding to the index finger fingertip. Display 400 provides a real-time read-out 410 of the pressure sensor output, such as a numerical voltage, numerical pressure, or numerical force by connection 420, which may be a wireless connection or a wired connection between the sensor and display. The sensor 100 is positioned so that it is between the portion of the hand or finger applying the force and the surface upon which the force is applied. In this fashion, a medical caregiver can easily and instantaneously have a quantitative measure of the force the caregiver is applying to a surface, such as a biological surface, including a tissue, an organ, or surface of a patient.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a sensor number, volume or size range, temperature range, a length range, a time range, a velocity, a pressure or rates thereof, a composition, or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Clinical data summary

| Patient | Sex | Age | BMI | PAD N. | VLPP | UPP | P det Q Max | Q max (free flow) | PVR | Baseline New Device Measure | Stop Leakage Measure |
|---|---|---|---|---|---|---|---|---|---|---|---|
| 1 | F | 55 | 23 | 1 | 65 | 25 | 11 | 19 | 240 | 0-3 | 12-16 |
| 2 | M | 67 | 31 | 0 | — | — | 33 | 7 | — | 2-5 | — |
| 3 | F | 66 | 28 | 4 | — | — | — | — | 0 | 0-2 | 11-38 |
| 4 | M | 74 | 25 | 0 | — | — | 120 | 5 | 113 | 0-8 | — |
| 5 | F | 60 | 30 | 3 | 40 | 20 | 40 | 20 | 0 | 0-5 | 15-30 |
| 6 | M | 55 | 27 | 2 | 60 | 30 | 50 | 18 | 50 | 0-9 | 14-25 |

BMI: Body Mass Index
PAD N.: number of diapers used per day
VLPP: Valsalva Leak Point Pressure (measured in cm $H_2O$)
UPP: urethral pressure profile (measured in cm $H_2O$)
Pdet Q Max: Pressure at Maximum Flow rate (measured in cm $H_2O$)
Q Max (free flow): Maximum free flow-rate
PVR: post void residual (amount of urine in bladder after voiding)
Baseline New Device Measure: Baseline measure of the pressure when the sensor is applied on the urethral surface
Stop Leakage Measure: The reading from the pressure sensor under the desired or optimal force applied to the urethra (the range corresponds to the minimum pressure required to stop leakage and the maximum pressure that stops flow referred herein as the "working pressure range").

We claim:

1. A method for treatment of urinary stress incontinence of a patient, the method comprising the steps of:
   introducing a force or a pressure sensor system on a skin surface of the patient adjacent to the urethra of the patient at a first time in a non-surgical clinical setting, wherein the force or pressure sensor system comprises a force or pressure sensor;
   applying an application force or pressure onto the force or the pressure sensor system and the underlying urethra in the non-surgical clinical setting, wherein the application force or pressure is sufficient to temporarily alleviate a urinary stress incontinence symptom and the force or pressure sensor is positioned between the application force or pressure and the urethra;
   identifying a clinically-derived an alleviation output from the force or pressure sensor on the skin surface corresponding to a minimum force or pressure sufficient to alleviate the urinary stress incontinence symptom in the non-surgical clinical setting;
   inserting a surgical sling to support the urethra in a surgical setting;

positioning the force or pressure sensor system to determine a force or pressure exerted by the surgical sling on the urethra at a second time in the surgical setting, wherein the second time in the surgical setting is after the first time in the non-surgical clinical setting;

exerting a force or pressure on the urethra by generating a force or pressure on the surgical sling in the surgical setting, wherein the exerted force or pressure is detected by the force or pressure sensor; and matching the exerted force or pressure on the urethra in the surgical setting to the clinically-derived alleviation output in the non-surgical clinical setting, thereby obtaining selecting an optimal generated force or pressure by the surgical sling in the surgical setting, wherein the optimal generated force or pressure by the surgical sling in the surgical setting at the second time is within about 20% of the clinically-derived alleviation output of the identifying step at the first time, thereby treating urinary stress incontinence of the patient.

2. The method of claim 1, wherein the force or pressure sensor system comprises:
   a microcontroller operably connected to the force or pressure sensor for processing the output from the force or pressure sensor; and
   a display operably connected to the microcontroller for displaying the processed output in real-time.

3. The method of claim 2, wherein the force or pressure sensor has a footprint area that is less than or equal to 1 cm$^2$ or a maximum transverse length that is selected from a range that is greater than or equal to 5 mm and less than or equal to 1 cm.

4. The method of claim 1, wherein the force or pressure sensor is positioned between the sling and the urethra, further comprising the step of removing the force or pressure sensor by sliding the force or pressure sensor out from between the sling and the urethra after the sling optimal generated force is selected.

5. The method of claim 1, wherein the force or pressure sensor provides real-time output by displaying said output from the force or pressure sensor to a display.

6. The method of claim 1, wherein the positioning step comprises temporarily affixing the force or pressure sensor to the surgical sling or to the urethra.

7. The method of claim 1, wherein the alleviation output corresponds to a working force or pressure range that is greater than or equal to a force or pressure sufficient to stop leakage and is less than a force or pressure that stops flow in the urethra.

8. The method of claim 1, wherein the force or pressure sensor is affixed to an object that applies the application force to the urethra.

9. The method of claim 1, further comprising the step of:
   selecting an input parameter that is matched to a sensitivity range of the force or pressure system to provide sensitivity over a desired application force range;
   wherein the application force or pressure is within the desired application force range and the input parameter is a driving voltage, a reference resistance, or both, and the application force range is up to 10 pounds of applied force.

* * * * *